(12) United States Patent
Sakai

(10) Patent No.: US 8,177,752 B2
(45) Date of Patent: May 15, 2012

(54) MEDICAL TUBE SET

(75) Inventor: Yosuke Sakai, Fukuroi (JP)

(73) Assignee: Tyco Healthcare Group LP, Mansfield, MA (US)

( * ) Notice: Subject to any disclaimer, the term of this patent is extended or adjusted under 35 U.S.C. 154(b) by 0 days.

(21) Appl. No.: 11/682,916

(22) Filed: Mar. 7, 2007

(65) Prior Publication Data
US 2007/0213672 A1 Sep. 13, 2007

(30) Foreign Application Priority Data

Mar. 9, 2006 (JP) ................................. 2006-063827

(51) Int. Cl.
*A61M 31/00* (2006.01)
*A61M 5/178* (2006.01)

(52) U.S. Cl. .................... 604/164.01; 604/509

(58) Field of Classification Search ............. 604/164.01, 604/164.06, 166.01, 164.03, 277, 27
See application file for complete search history.

(56) References Cited

U.S. PATENT DOCUMENTS

| | | | |
|---|---|---|---|
| 4,790,817 A * | 12/1988 | Luther | 604/509 |
| 5,041,093 A * | 8/1991 | Chu | 604/104 |
| 5,447,503 A | 9/1995 | Miller | |
| 6,210,370 B1 * | 4/2001 | Chi-Sing et al. | 604/164.03 |
| 6,866,655 B2 * | 3/2005 | Hackett | 604/264 |
| 6,979,343 B2 * | 12/2005 | Russo et al. | 606/200 |
| 7,029,488 B2 * | 4/2006 | Schonholz et al. | 606/200 |
| 7,252,675 B2 * | 8/2007 | Denison et al. | 606/200 |
| 2002/0010476 A1 * | 1/2002 | Mulholland et al. | 606/108 |
| 2005/0288764 A1 * | 12/2005 | Snow et al. | 623/1.11 |

FOREIGN PATENT DOCUMENTS

| | | | |
|---|---|---|---|
| JP | 09084880 A | | 3/1997 |
| JP | 10151195 A | * | 6/1998 |
| JP | 2000024105 A | * | 1/2000 |
| WO | 00/44428 A1 | | 8/2000 |

OTHER PUBLICATIONS

Extended European Search Report dated Apr. 27, 2007.

* cited by examiner

*Primary Examiner* — Kevin C Sirmons
*Assistant Examiner* — Bradley Osinski
(74) *Attorney, Agent, or Firm* — Elias Domingo, Esq.

(57) ABSTRACT

A medical tube set includes a tube and a stylet that improves the insertability of tube. The stylet structure comprises an inner core that can be inserted into the tube, an apical tip that is affixed to the apical end of inner core, and a movable expansion member that can move between apical tip of inner core and stop that is provided at a predetermined distance from apical tip. An engagement is formed at the posterior end of apical tip, and is able to engage the apical end of tube. By positioning movable expansion member within apical end of tube, apical end can expand radially outwards so that apical tip can pass through.

14 Claims, 16 Drawing Sheets

MEDICAL TUBE SET

FIELD OF THE INVENTION

The present invention generally relates to a medical tube set and a method for inserting a medical tube set in a patient.

BACKGROUND OF THE INVENTION

Conventionally, for example, the drainage of residuum from inside the colon of patients with ileus was conducted by inserting a tube from the anus and allowing this to indwell. As the tube used in this case, some are inserted into the body via a guide wire (for example cf. Japanese Kokai Patent Application No. Hei 10[1998] 151195). When this tube is inserted into the body, a colon fiberscope is inserted from the anus, and a guide wire is inserted into the colon fiberscope. Then, after the colon fiberscope has been removed from the anus, the tube's apical, or distal, end aperture is put into the posterior end of the guide wire, and the operation of inserting the tube into the body is conducted such that it follows along the guide wire.

Nevertheless, the operation for inserting the tube into the body and allowing it to indwell is troublesome with the aforementioned tube. Moreover, with conventional stylets, when force is applied to the distal end of the stylet so as to push the stylet towards the inside of the tube, it sometimes happens that the stylet's distal end is pushed into the inside of the tube.

SUMMARY OF THE INVENTION

In one aspect of the present invention, a medical tube set generally comprises a tube for insertion into a patient and a stylet disposed within the tube. The stylet comprises a core unit and an apical tip unit attached to a distal end of the core unit. The apical tip unit is arranged to engage with a distal end of the tube for insertion of the tube and stylet into a patient. The stylet further comprises an expansion member movable with respect to the core unit such that the expansion member is deployable to expand the distal end of the tube so as to allow retraction of the stylet from the tube.

In another aspect, a method for inserting a medical tube set into a patient generally comprises the step of inserting a tube into a patient to a desired position wherein a distal end of said tube is engaged with an apical tip unit of a stylet disposed within the tube. A core unit of the stylet is pushed in a distal direction causing an expansion member located on the core unit to expand a distal end of the tube. The core unit is pulled in a proximal direction such that the apical tip unit engages with the expansion member. The stylet is withdrawn from the tube.

Other features will be in part apparent and in part pointed out hereinafter.

BRIEF DESCRIPTION OF THE DRAWINGS

Corresponding reference characters indicate corresponding parts throughout the drawings.

DETAILED DESCRIPTION OF THE DRAWINGS

Figure 1:
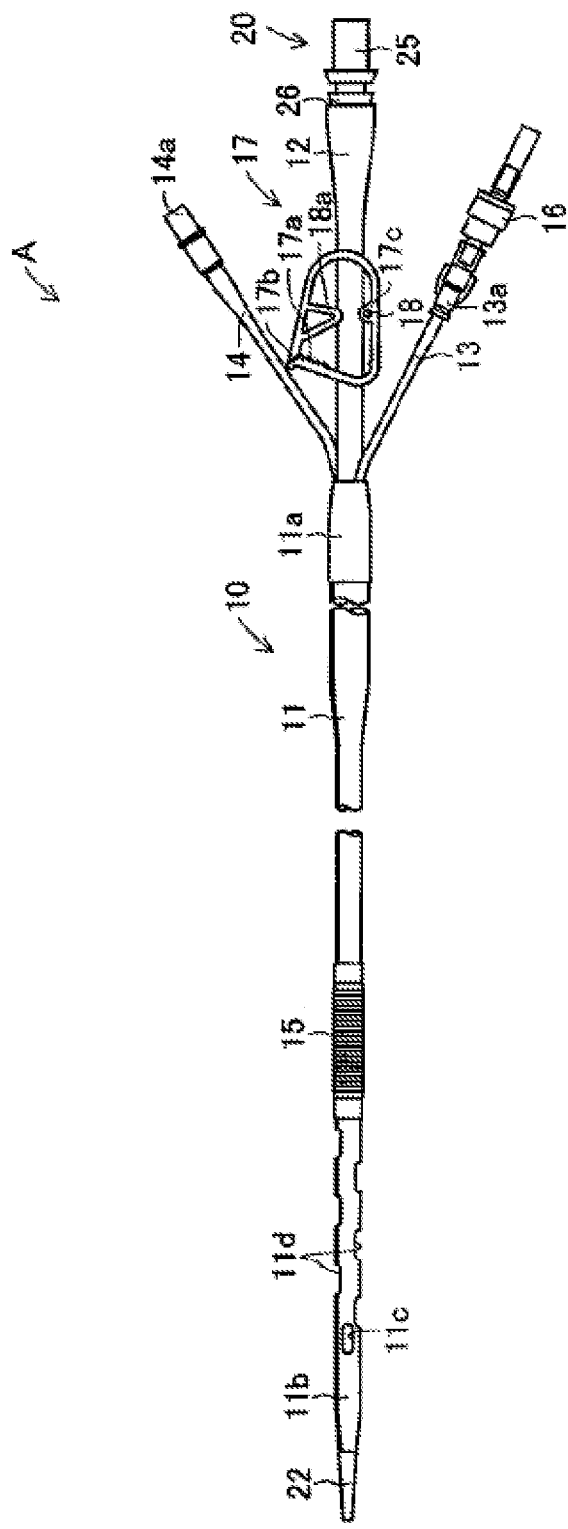
FIG. 1 is a side view showing the medical tube set of the first embodiment of the invention.
Figure 2:
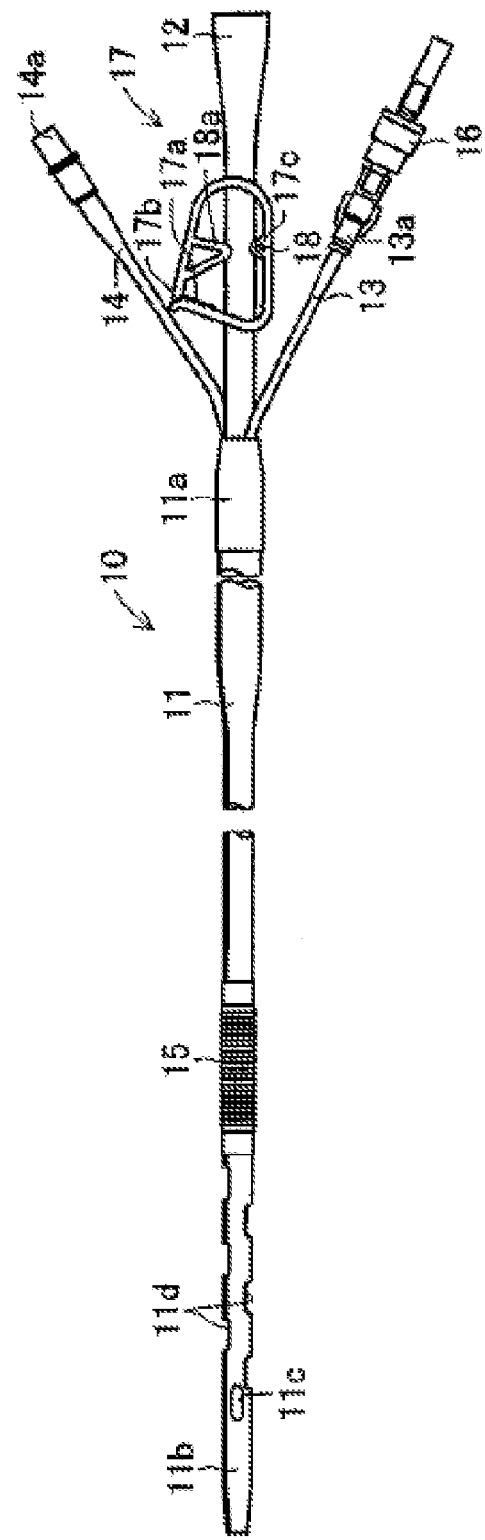
FIG. 2 is a side view of the tube provided for the medical tube set shown in FIG. 1.

The following statements explain the invention in greater detail using drawings of a first embodiment of the invented medical tube set. FIG. 1 shows tube set A for medical use in the same embodiment. The medical tube set A is used to drain residuum remaining in the part positioned beyond a constriction K (affected area), as considered from the rectum, developed within the colon T of the patient (cf. FIG. 7 and FIG. 8); it comprises a tube 10, indwelling in colon T, and a detachable stylet 20 that is attached inside tube 10. As shown in FIG. 2, tube 10 comprises a tube main unit 11, comprising a long, thin tube, and three branch tubes 12, 13, and 14 that branch off from the basal end 11a of tube main unit 11.

The distal end 11b of tube main unit 11 is formed as a cylinder with a slightly tapered front end, with irrigation side hole 11c being formed close behind distal end 11b on the circumference of tube main unit 11. Also, multiple flushing side holes 11d are formed close behind irrigation side hole 11c on the circumference of tube main unit 11, along the axial direction, with variation of the circumferential position. An imaging balloon 15, which is expandable and contractable, is provided close behind flushing side holes 11d on the circumference of tube main unit 11.

Inside tube main unit 11a main cavity 11e (cf. FIG. 4 through FIG. 6) is formed, which has a large diameter that, from the aperture of distal end 11b, passes through the posterior end aperture of branch tube 12 via the basal end 11a. Although it is not shown in the figures, two small sub cavities are formed on both sides, within a cross section of main cavity 11e, inside tube main unit 11. One sub cavity passes through branch tube 13 from irrigation side hole 11c via basal end 11a, and the other sub cavity passes through branch tube 14 from imaging balloon 15 via basal end 11*a*. Multiple flushing side holes 11*d* pass though the main cavity.

It is possible to connect a suction device, such as a waste fluid bag, for example, or an irrigation liquid supply device such as a syringe, for example, to the posterior end of branch tube 12, via a Y shaped connector tube (not shown in the drawings). This makes it possible to suction and remove the residuum from inside colon T via the distal end aperture of distal end 11*b* and flushing side holes 11*d*. The irrigation side hole 11*c* releases air supplied from branch tube 13 inside the body; this provision permits either the injection of a contrast medium, or the supply of air inside colon T which has become depressurized due to suction by the suction device, via main cavity 11*e*, for example.

A supply device (not shown in the drawings), such as a syringe, for example, supplies water to rear tip 14*a* of branch tube 14, and the imaging balloon 15 enlarges due to the water supplied from the supply device via branch tube 14, thus fixing the front tip portion of tube main unit 11 at a predetermined part inside colon T. The imaging balloon 15 is formed from a material with which an impermeable substance, through which x rays cannot pass, is kneaded into an expandable and contractible elastic resin, thus obtaining a structure that allows images to be taken by X ray radiation. Accordingly, when medical tube set A is inserted inside the patient's colon T, it is possible to accurately know the position of the front tip portion of medical tube set A.

The branch tube 13 structure comprises a tube having a smaller diameter than branch tube 12, with a backflow valve 16 attached to its posterior end 13*a*. The backflow valve 16 is structured such that air will pass through branch tube 13 from the outside, but air and other fluids will not pass from the inside of branch tube 13 to the outside. Thus the backflow valve 16 prevents release of the residuum from inside the patient's colon T to the outside via irrigation side hole 11*c*, sub cavities, or branch tube 13. The branch tube 14 structure comprises a tube having approximately the same diameter as branch tube 13, with a supply device such as a syringe, for example, being attached to its rear tip 14*a* in order to send water to imaging balloon 15. The imaging balloon 15 can be suitably expanded by operating this supply device.

In the approximate center of branch tube 12, clamp 17 has been attached in order to adjust the flow rate into the inner cavity by squeezing the inner cavity or closing the inner cavity of branch tube 12. The clamp 17 is formed by bending a long, thin plate shaped body into an approximately square frame provided with elasticity; an engagement member 17*a* comprising several steps is formed within the inner surface of the end portion, and the other end tip 17*b* is formed suitable to engage a predetermined portion of engagement member 17*a*. Before and after clamp 17 apertures (not shown in the drawings) have been formed to permit the insertion and passage of the branch tube 12, branch tube 12 is inserted into both apertures, and clamp 17 is attached to branch tube 12.

Support leaves 17*c* are provided on both sides of the inner surface of the lower central part of clamp 17, and pin 18 bridges the two support leaves 17*c*. On both inner sides of the upper central part of clamp 17, pressure leaves 18*a* are formed and project toward pin 18. Accordingly, by changing the engagement position of tip 17*b* of engagement member 17*a*, it is possible to change the interval between pin 18 and pressure leaves 18*a*, and thus to change the size of the space within branch tube 12 or to close it off, and thus to regulate the flow rate.

Figure 3:
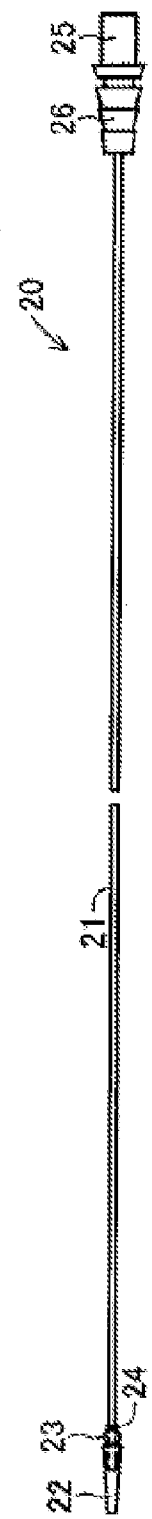
FIG. 3 is a side view of the stylet provided for the medical tube set shown in FIG. 1.
Figure 4:
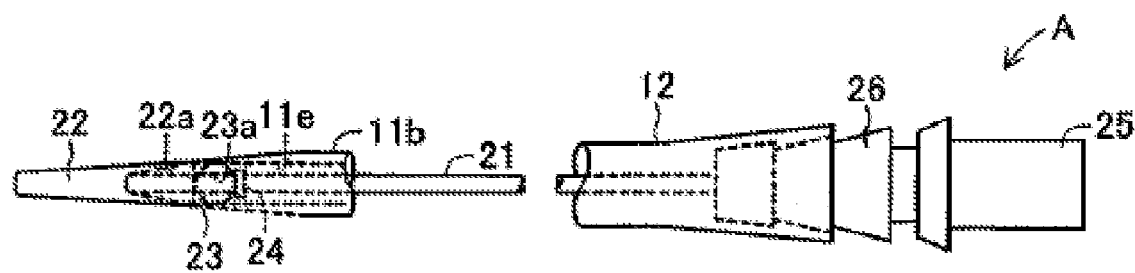
FIG. 4 is a side view of the essentials of a medical tube set.
Figure 5:
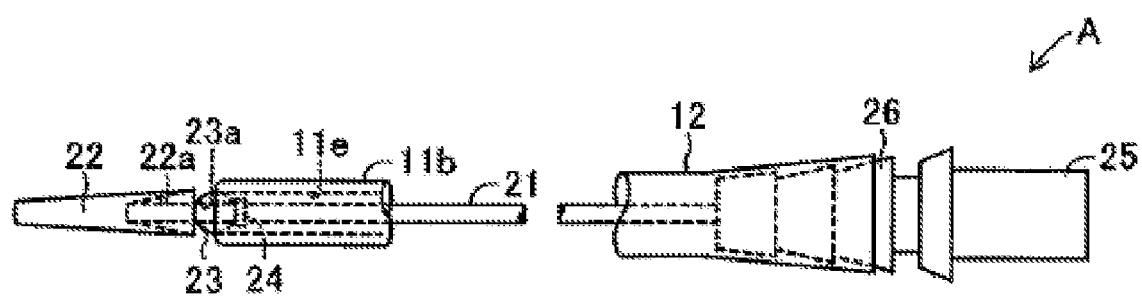
FIG. 5 is a side view showing the essentials of a medical tube set in a condition where the apical tip is projecting from the distal end of the tube main unit.
Figure 6:
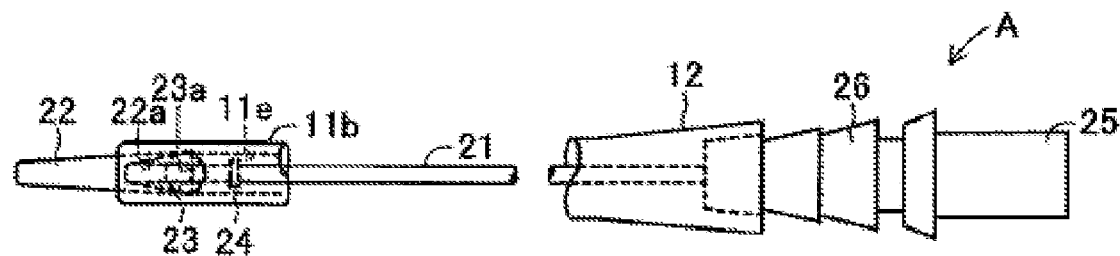
FIG. 6 is a side view showing the essentials of a medical tube set in a condition where the apical tip has been placed into the distal end of the tube main unit.

As shown in FIG. 3, stylet 20 is provided with an inner core 21 insertable into tube main unit 11 and branch tube 12, an apical tip 22 affixed to the distal end of inner core 21, and a mobile expansion member 23 that can move along inner core 21 to the posterior part of apical tip 22 in inner core 21. As shown in FIG. 4 through FIG. 6, the apical tip 22 has a truncated conical shape, with the distal end narrowing from the posterior end, while the posterior end is formed into an engagement concavity 22*a* that can engage with aperture rim of distal end 11*b* of tube main unit 11.

The mobile expansion member 23 is formed as a sphere provided with insertion through hole 23*a* that passes through from front to back; mobility along inner core 21 is possible by passing inner core 21 by insertion through hole 23*a*. The diameter of mobile expansion member 23 is established to be slightly larger then the inner diameter of the distal end aperture of distal end 11*b* of tube main unit 11; by positioning the mobile expansion member 23 within the distal end aperture of distal end 11*b*, the distal end aperture of distal end 11*b* expands radially outwards. The diameter of mobile expansion member 23 is established so as to be slightly larger than the posterior end of apical tip 22; approximately the front half of mobile expansion member 23 enters engagement concavity 22*a* of apical tip 22, and engages with apical tip 22.

When mobile expansion member 23 and apical tip 22 are engaged, the formation of apical tip 22 and mobile expansion member 23 produces almost no stepwise difference at the interface between mobile expansion member 23 and the aperture rim of engagement concavity 22*a*. In the part where a predetermined distance is maintained from apical tip 22 in inner core 21, a stop 24 is provided in order to regulate the final part of the mobile range of mobile expansion member 23. A cylindrical grip 25 is provided on the posterior end of tube main unit 11; a stepwise-tapering engagement member 26, formed with tapered stages that engages with the posterior end aperture of branch tube 12, is provided on the forward side of grip 25.

Given this structure, when medical tube set A is used to drain the residuum from inside the patient's colon T, clamp 17 is first loosened and stylet 20 is inserted, beginning from apical tip 22, from the posterior end aperture of branch tube 12 of tube 10, thus giving the condition shown in FIG. 1. In this case, as shown in FIG. 4, mobile expansion member 23 comes into contact with stop 24, thus being positioned at the terminus of the mobility range along inner core 21, in a condition where the aperture rim of distal end 11*b* of tube main unit 11 is engaged with engagement concavity 22*a* of apical tip 22. Also, the stepwise-tapering engagement member 26 is engaged with the posterior end of branch tube 12.

Figure 7:
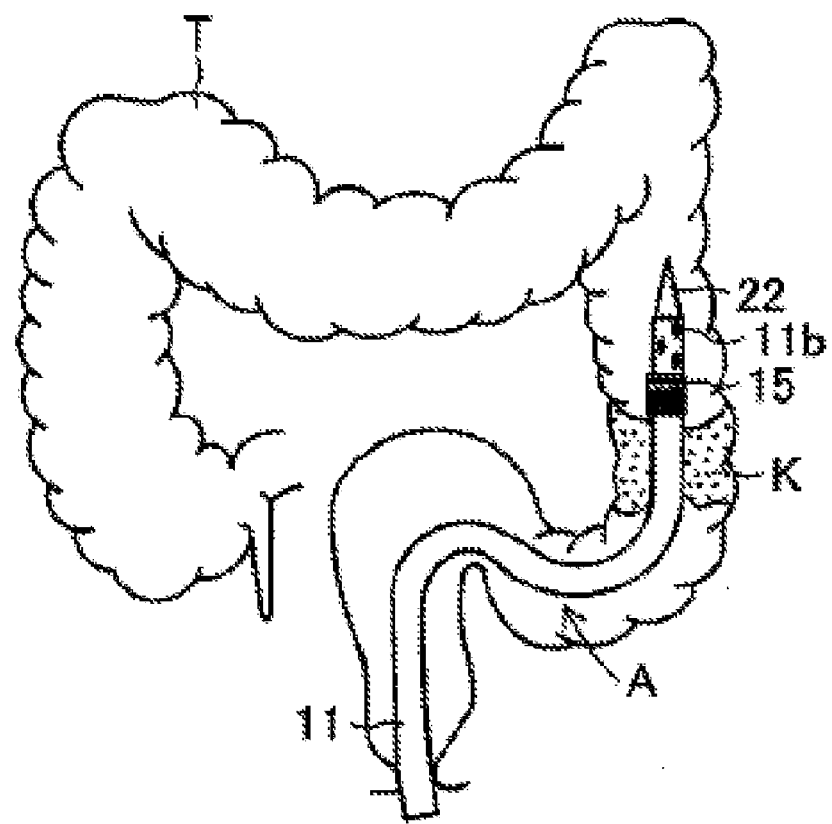
FIG. 7 is an explanatory diagram showing a condition where a medical tube set has been inserted into the colon.

Then the medical tube set A is inserted inside colon T, from apical tip 22, and passes beyond constriction K, as shown in FIG. 7. At this time, the patient's body is x rayed, and by seeing through imaging balloon 15, its location is confirmed. Because apical tip 22 of stylet 20 tapers, medical tube set A is easily inserted while widening constriction K. When the apical tip 22 of medical tube set A reaches the predetermined affected area inside colon T, stylet 20 is removed from tube 10. In this case, as shown in FIG. 5, the grip 25 of stylet 20 is temporarily pushed towards the inside of tube 10, causing apical tip 22 to project from distal end 11*b* of tube main unit 11. Then mobile expansion member 23 pushes against stop 24 and moves together with the other part of stylet 20, thus causing the expansion of the distal end aperture of distal end 11*b* of tube main unit 11.

Then grip 25 of stylet 20 is pulled backwards and out of tube 10. The mobile expansion member 23 is arrested by friction against the aperture rim of distal end 11*b*, while the other part of stylet 20 is withdrawn backwards through tube 10. While mobile expansion member 23 is engaged in engagement concavity 22a of apical tip 22, mobile expansion member 23 forms a single unit with apical tip 22 and enters tube main unit 11. Then, due to mobile expansion member 23, the distal end aperture of distal end 11b becomes enlarged, and since a stepwise difference is not present between apical tip 22 and mobile expansion member 23, the apical tip 22 will smoothly enter tube main unit 11 without catching on the aperture rim of distal end 11b, thus presenting the condition shown in FIG. 6.

In this condition, stepwise-tapering engagement member 26 is withdrawn from the posterior end of branch tube 12 and the engagement is cleared. Thus, by pulling grip 25 of stylet 20 to the outside of tube 10, it is possible to easily remove stylet 20 from tube 10. In this way, after medical tube set A has been inserted inside colon T, stylet 20 is removed from tube 10, which makes it possible to reduce the occurrence of colon puncture.

Figure 8:
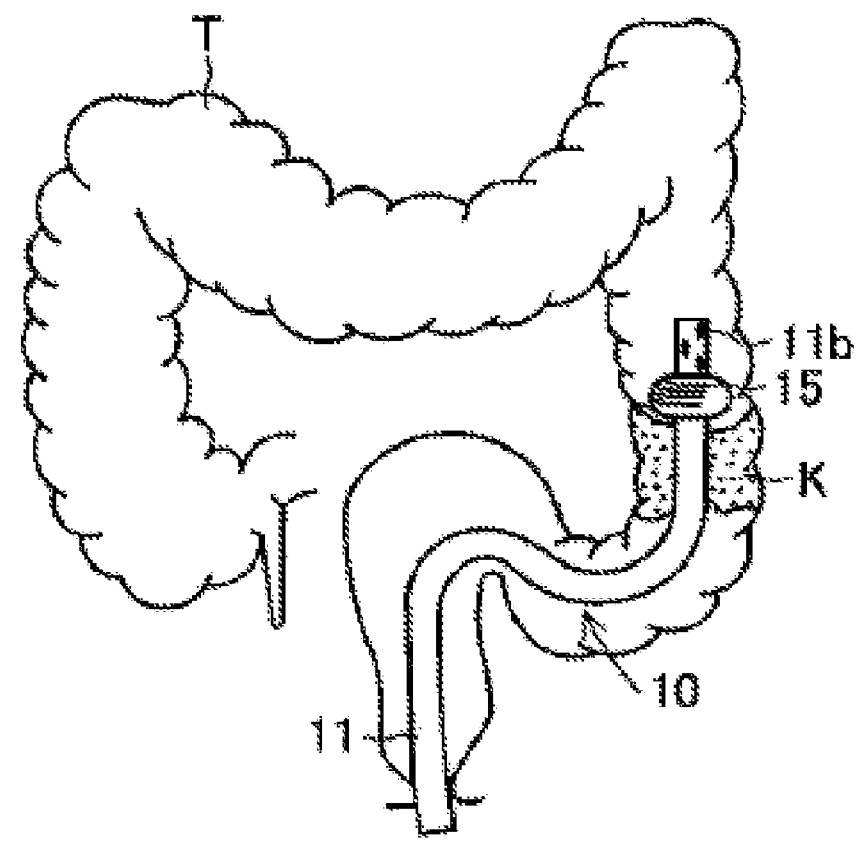
FIG. 8 is an explanatory diagram showing a condition where a tube is indwelling in the colon.

Then the suction device and irrigation liquid supply device are connected to the posterior end of branch tube 12, and a water supply device is connected to the posterior end of branch tube 14. The water supply device is then operated (in the case of a syringe, this means pushing the plunger), thus supplying water into imaging balloon 15. Thus, imaging balloon 15 expands, and exerts pressure against the inner wall of colon T, or comes into close contact with constriction K, thus fixing distal end 11b of tube 10, as shown in FIG. 8. If a contrast medium is injected into colon T via irrigation side hole 11c, since the pressure of imaging balloon 15 causes the tube 10 to be fixed against the inside wall of colon T or against constriction K, contrast medium out of the anus is prevented from leaking.

Then the irrigation liquid supply device is activated to supply irrigation liquid into colon T, and the suction device is activated to suck and remove the mixture of residuum and irrigation liquid inside colon T. By this means, the residuum from inside colon T is gradually drained. When this happens, air is supplied from branch tube 13 so that negative pressure will not develop inside colon T. The backflow valve 16 prevents the residuum from inside colon T from flowing backwards through branch tube 13 and being released to the outside. During the time that irrigation liquid is being supplied into colon T and the mixture of residuum and irrigation liquid in colon T is being suctioned and removed, the flow rate is regulated by clamp 17. Once all the residuum from inside colon T has been drained, tube 10 is removed from the patient's body. At this time, tube 10 is put in a condition such that imaging balloon 15 is shrunk, by withdrawing the water in imaging balloon 15, so it can be pulled out of the body and removed.

In this way, medical tube set A of the present embodiment comprising stylet 20, which is used to improve the insertion characteristics when tube 10 is inserted into the body, provides an apical tip 22 in which engagement concavity 22a is formed at the posterior end to which the distal end of inner core 21 is affixed, and also provides a mobile expansion member 23 that can move between apical tip 22 and stop 24 along inner core 21. Thus, when medical tube set A is inserted into colon T, the aperture rim of distal end 11b of tube main unit 11 becomes engaged with engagement concavity 22a of apical tip 22, thereby positioning mobile expansion member 23 within distal end 11b. This allows insertion of medical tube set A into colon T and prevents apical tip 22 from entering tube main unit 11.

After medical tube set A has been inserted into colon T and it is time to remove stylet 20 from tube 10, grip 25 of stylet 20 is pushed in from the posterior end of tube 10 towards the distal end, which releases the engagement between apical tip 22 and the distal end 11b of tube main unit 11 and also causes the distal end aperture of distal end 11b of tube main unit 11 to expand radially outwards because of mobile expansion member 23. Then, by pulling stylet 20 towards the posterior end, it can be removed from tube 10. The external diameter of mobile expansion member 23 is larger than the external diameter of apical tip 22, so mobile expansion member 23 and apical tip 22 smoothly enter the distal end of tube 10.

The part of tube main unit 11 other than the distal end aperture of distal end 11b is thicker than the distal end aperture, so that after mobile expansion member 23 and apical tip 22 have been put inside the distal end of tube 10, stylet 20 moves smoothly towards the posterior end. Also mobile expansion member 23 is structured as a spherical member, which has the advantages of making the structure of mobile expansion member 23 simple, and of permitting a reliable removal operation for stylet 20. The provision of stop 24 at a part of inner core 21 at a predetermined distance from apical tip 22 enables movement of mobile expansion member 23 between apical tip 22 and stop 24, which allows regulation, by a simple structure, the range of mobility of mobile expansion member 23 with respect to inner core 21.

FIGS. 9 through 14 show the essentials of medical tube set B of a second embodiment of the invention. In medical tube set B, the distal end 31b of tube main unit 31 is formed in an approximately cylindrical tapered shape with the diameter decreasing towards the distal end. The portion of inner core 41 corresponding to the posterior end of apical tip 42 is provided with a disk shaped stop 44, co axial with inner core 41, which regulates the farthest forward portion of the movement range of mobile expansion member 43. The other components of medical tube set B are identical to medical tube set A of the aforementioned first embodiment of the invention. Accordingly, identical parts are indicated by identical keys, and explanations are omitted.

Figure 9:
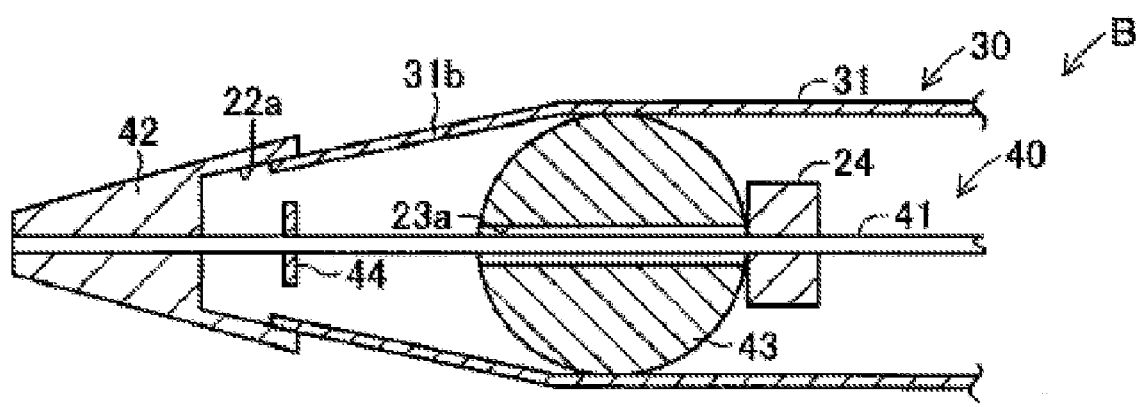
FIG. 9 is a cross section showing the essentials of a medical tube set of the second embodiment of the invention.
Figure 10:
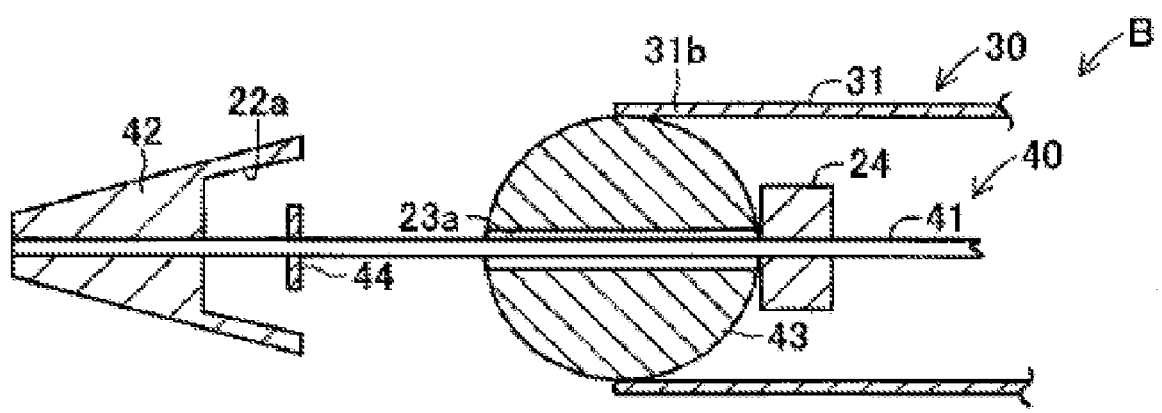
FIG. 10 is a cross section showing the condition wherein the apical tip of the medical tube set of FIG. 9 is projecting from the distal end of the tube main unit.

When medical tube set B is inserted into the patient's colon T, the front tip of medical tube set B has the condition shown in FIG. 9. After medical tube set B has been inserted into colon T and the time comes to remove stylet 40 from tube 30, first the posterior end of stylet 40 is pushed towards the inside of tube 30, which causes apical tip 42 to project from distal end 31b of tube main unit 31, as shown in FIG. 10. At this time, mobile expansion member 43 is pushed by stop 24, and moves together with the other parts of stylet 40, causing distal end 31b of tube main unit 31 to enlarge and to assume approximately the same radius as the other part.

Figure 11:
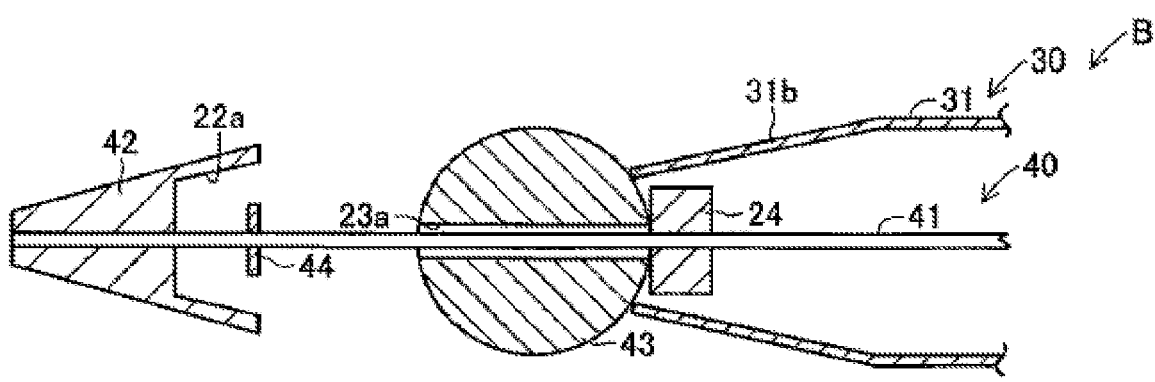
FIG. 11 is a cross section showing the condition wherein the mobile expansion member of the medical tube set of FIG. 10 is being thrust out of the distal end of the tube main unit.
Figure 12:
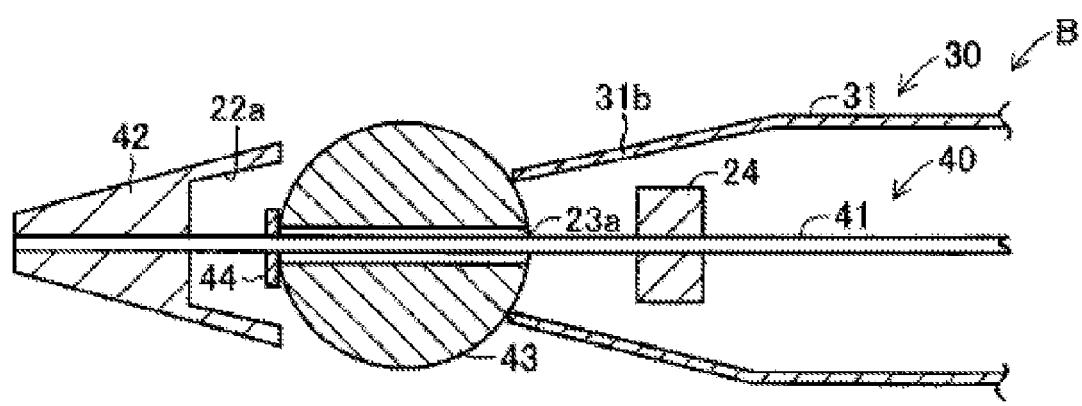
FIG. 12 is a cross section showing the condition wherein the stylet of the medical tube set of FIG. 11 has been pulled backwards.

Then the posterior end of stylet 40 is further pushed towards the inside of tube 30, as shown in FIG. 11, causing the mobile expansion member 43 to project outwards from distal end 31b of tube main unit 31 and apical tip 42 to be thrust even farther forward. Then stylet 40 is pulled towards the rear of tube 30. In this case, mobile expansion member 43 assumes an arrested condition, being blocked by the aperture rim of distal end 31b, whereas the other part of stylet 40 is withdrawn from tube 30. The stop 44 comes into contact with mobile expansion member 43 giving the condition shown in FIG. 12.

Figure 13:
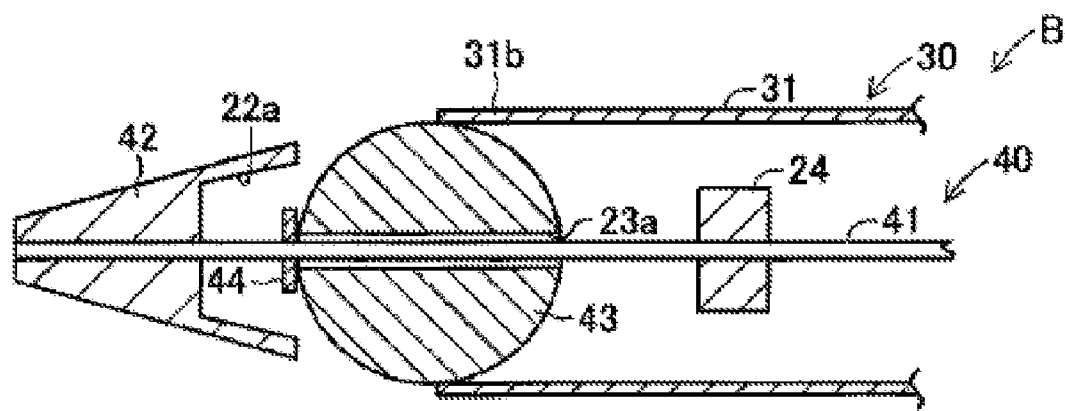
FIG. 13 is a cross section showing the condition wherein the stylet of the medical tube set of FIG. 12 has been pulled backwards, causing the mobile expansion member to be positioned at the aperture of the tube main unit.
Figure 14:
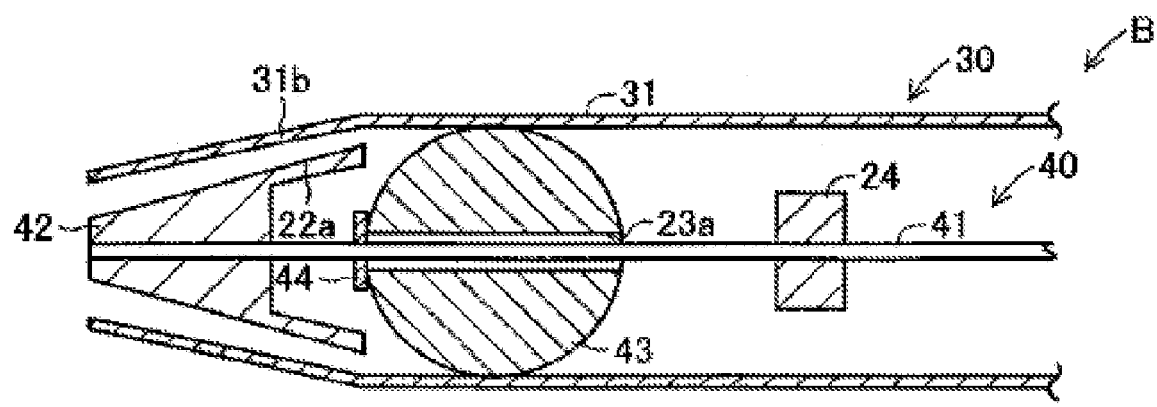
FIG. 14 is a cross section showing the condition wherein the stylet of the medical tube set of FIG. 13 has been pulled backwards, causing the apical tip to go inside the tube main unit.

When stylet 40 is withdrawn backwards through tube 30, as shown in FIG. 13, the mobile expansion member 43 causes distal end 31b to enlarge, and forms a single unit with apical tip 42, entering into tube main unit 31. Then as shown in FIG. 14, when stylet 40 is withdrawn toward the rear of tube 30, the mobile expansion member 43 and apical tip 42 enter distal end 31b, and distal end 31b then returns to its original tapered shape. Then stylet 40 can be removed from tube 30 by further withdrawing stylet 40 backwards through tube 30.

According to medical tube set B, the distal end 31*b* of tube main unit 31 is formed in a slightly acute tapered shape, and thus, it can be securely engaged in engagement concavity 22*a* of apical tip 42. Provision is made for a stop 44 at the portion of inner core 41 that corresponds to the posterior part of apical tip 42, which makes it possible to secure the stopping position of the distal end of mobile expansion member 43 in inner core 41. It is possible to prevent damage to apical tip 42, since mobile expansion member 43 is not pressed directly by apical tip 42. In other respects the operation and effect of medical tube set B are identical to the operation and effect of medical tube set A.

Figure 15:
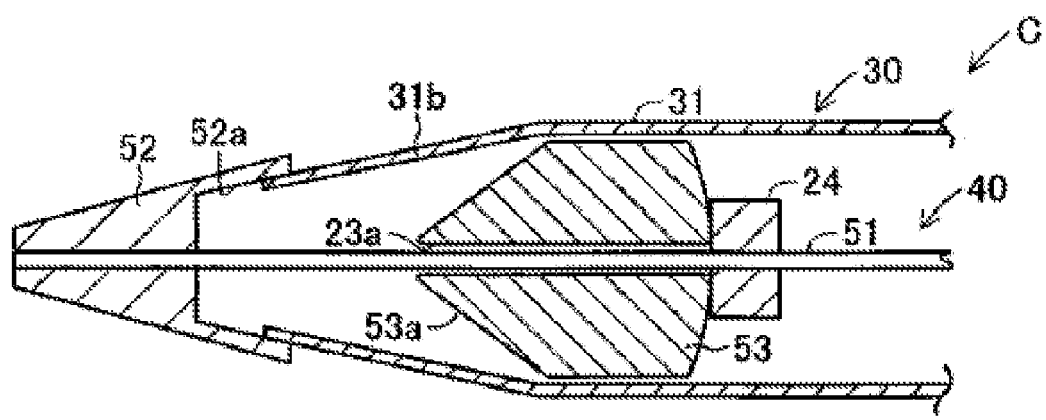
FIG. 15 is a cross section showing the essentials of a medical tube set pertaining to the third embodiment of the invention.

FIG. 15 shows the essential elements of medical tube set C of a third embodiment of the invention. For this medical tube set C the mobile expansion member 53 is not spherical; rather, the forward side portion is an engagement projection 53*a* of approximately conical shape that can engage with engagement concavity 52*a* of inner core 52, and the rearward portion has a gently curved surface. Also, a stop is not provided at the part that corresponds to the rearward part of apical tip 52 in inner core 51. The structure of the other parts of medical tube set C is identical to that of medical tube set B of the aforementioned second embodiment of the invention. Accordingly, identical parts are indicated by identical keys, and explanations are omitted.

Given this structure, stylet 40 is pushed into tube 30 from the posterior end towards the distal end, causing mobile expansion member 53 to be thrust out of distal end 31*b* of tube main unit 31; subsequently when stylet 40 is pulled towards the back of tube 30, the engagement concavity 52*a* of apical tip 52 engages with engagement projection 53*a* of mobile expansion member 53. Because of this, apical tip 52 and mobile expansion member 53 become a single unit, and are able to move. This enables the smooth removal of stylet 40 from tube 30. When mobile expansion member 53 projects out of distal end 31*b* of tube main unit 31, the engagement projection 53*a* of mobile expansion member 53 causes distal end 31*b* to expand smoothly, without undue awkwardness. In other respects the operation and effect of medical tube set C are identical to the operation and effect of medical tube set B.

Figure 16:
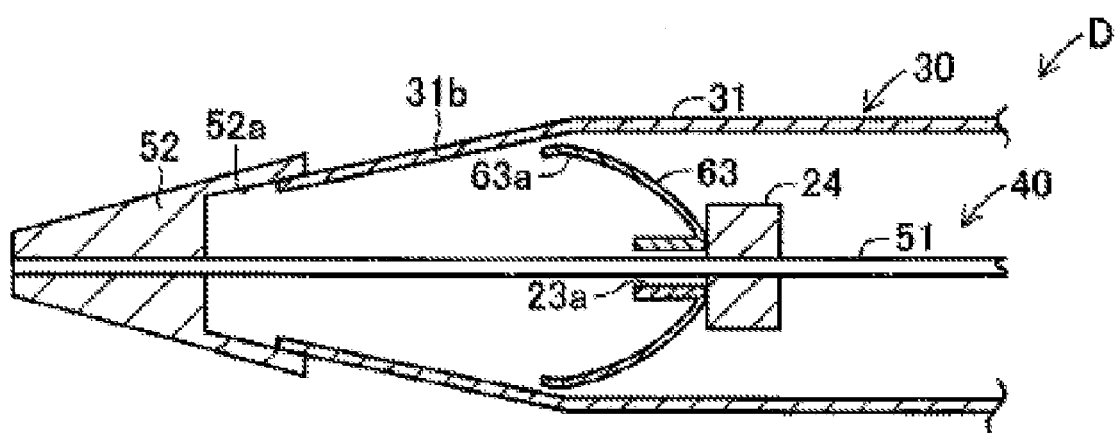
FIG. 16 is a cross section showing the essentials of a medical tube set pertaining to the fourth embodiment of the invention.

FIG. 16 shows the essentials of medical tube set D of a fourth embodiment of the invention. In medical tube set D, mobile expansion member 63 is formed into a dome shape that widens from the back to the front. More specifically, the distal end of mobile expansion member 63 is structured by an engagement covering 63*a* comprising a large open aperture part, and the outer circumference facing to the rear of mobile expansion member 63 has a curved plane. The structure of the other parts of medical tube set D is identical to that of medical tube set C of the previously described third embodiment of the invention. Accordingly, identical parts are indicated by identical keys, and explanations are omitted.

Given this structure, stylet 40 is pushed into the distal end of tube 30 causing mobile expansion member 63 to be thrust out of distal end 31*b* of tube main unit 31; subsequently, when stylet 40 is pulled towards the back of tube 30, the engagement covering 63*a* of mobile expansion member 63 covers the posterior end of apical tip 52, and in this condition mobile expansion member 63 engages with apical tip 52. Because of this, when viewed from the direction of movement of mobile expansion member 63 and apical tip 52, the apical tip 52 is covered by mobile expansion member 63 and thus is unseen, and the removal of stylet 40 from tube 30 will be even smoother. In other respects the operation and effect of medical tube set D are identical to the operation and effect of medical tube set C.

The invented medical tube set is not limited to the embodiments described above, but may be realized by making suitable changes. For example, in the aforementioned embodiments the distal end 11*b*, for example, of tube main unit 11, for example, was tapered, but, for example, distal end 11*b* can have a cylindrical shape with the same diameter as other parts. In this case, the distal end aperture of distal end 11*b*, for example, is caused to contract and then engage with apical tip 22, for example. It is also possible to provide a slit along the axial direction of distal end 11*b*, for example, to facilitate engagement of distal end 11*b*, for example with apical tip 22, for example.

Furthermore, in the aforementioned medical tube set D, the engagement covering 63*a* of mobile expansion member 63 covered the posterior end of apical tip 52, but the size of mobile expansion member 63 can be increased so as to cover the entire body of apical tip 52. In the embodiments described above, at least one stop 24 or 44 comprising an element different from inner core 21 was provided and the stop 24 or 44 was affixed to the inner core 21, for example, but a large-diameter portion could be provided on the circumference of inner core 21, for example, and be used as a stop.

As can be seen from the illustrated embodiments, a method has been investigated wherein a stylet for improving the insertability of the tube is placed in the tube cavity. The tube and the stylet are inserted into the body together, and after the tube's apical end has passed beyond the constriction in the colon and reached the affected area within the body, the stylet is then removed from the tube. When the tube and stylet are inserted into the body together, it is necessary for the distal end of the stylet to be formed in a tapered shape, and for the distal end to project from the front end of the tube, in order for the insertion of the tube to proceed smoothly.

As can also be seen, investigations led to a device whereby provision is made for a stepwise difference between the tube's distal end aperture and the projecting portion of the front end of the stylet, so as to prevent the stylet's distal end from entering the tube. In order to reliably prevent the entry of the stylet's distal end into the tube, it is necessary to increase the stepwise difference between the type's distal end aperture and the projecting part of the stylet, but if this stepwise difference is too big, a problem of increased resistance appears when removing the stylet from the tube, and the resistance increases particularly when withdrawing the projecting part of the stylet from the tube's distal end aperture.

In keen awareness of this situation, at least one embodiment of the present invention offers a medical tube set that provides for a stylet that improves the insertability of the tube, and that is easy to use.

The structural characteristics of at least one embodiment of the medical tube set are a medical tube comprising a tube that is insertable into the body, and a stylet that is suitable to improve the insertability of the aforementioned tube when the aforementioned tube is inserted into the body; the stylet comprises an inner core that is insertable through the tube; an apical tip that is affixed to the distal end of the inner core, that covers the periphery of the distal end in the contracted condition of the tube at the posterior end, and that is formed with an engagement concavity that is engageable with the distal end of the tube; and a mobile expansion member which is moveable between the apical tip in the inner core that has been inserted into the inner core in a hole furnished in its interior and a portion positioned in a predetermined distance from the apical tip, which is provided with an external diameter that is either equal to or larger than the external diameter of the apical tip, and which, by being positioned within the distal end of the tube, expands the distal end of the tube in the contracted condition radially outwards, such that the apical tip passes through.

The medical tube set having the structure described above is operated as follows: when the medical tube set is inserted into the body, the engagement covering formed at the posterior end of the apical tip engaged with the aperture rim of the tube's distal end, and the mobile expansion member is positioned within the tube. By this means, the posterior end of the apical tip covers the periphery of the tube's distal end, so that even if a pushing force is applied to the apical tip towards the inside of the tube, the apical tip will not retreat backwards into the inside of the tube. The engagement covering of the apical tip is engaged in the distal end while the tube is contracted, so the external diameter of the apical tip does not need to be increased, nor is it necessary to provide a large stepwise difference between the posterior end of the apical tip and the tube's distal end. This improves the insertability of the medical tube set.

After the medical tube set has been inserted into the body and the time comes to withdraw the stylet from the tube, the stylet is pushed forward from the back of the tube towards the distal end, disengaging the tube's distal end from the engagement covering of the apical tip, and initiating radial outwards expansion of the distal end aperture of the tube by moving a mobile expansion member. At this time, the apical tip is in the condition of being thrust forwards from the distal end. Then the stylet is pulled to the rear of the tube, the mobile expansion member and apical tip are withdrawn, and, having entered into the tube's distal end, the stylet is drawn further backwards and removed from the tube.

When the time comes to pull the stylet backwards through the tube, the mobile expansion member is positioned in a place separated by a predetermined distance from the apical tip of the stylet, but due to friction with the distal end aperture of the tube, it is prevented from moving together with the stylet. After the mobile expansion member moves to a position where it comes into contact with the apical tip, in a condition where the tube's distal end has been expanded, it enters the tube's distal end together with the apical tip. In this case, because the external diameter of the mobile expansion member has been set equal to or larger than the external diameter of the apical tip, the mobile expansion member and apical tip smoothly enter the distal end of the tube.

The external diameter of the mobile expansion member and of the apical tip in this case refers to the respective diameter of the part where the diameter is at a maximum. According to this, and seen from the orientation of the mobile expansion member and apical tip movement, the stepwise difference between the mobile expansion member and apical tip is eliminated. Therefore, the removal of the stylet from the tube is smooth. Also, by this means, it is possible to remove the stylet from the tube reliably by a simple operation. It is also possible to form the tube's distal end into a tapered shape, so that it will expand radially outwards when passing through the mobile expansion member; and it is also possible for the posterior part to have approximately the same diameter, so that it contracts into a tapered shape when the apical tip and engagement concavity are engaged.

In this case, it is possible to provide a slit extending axially in the tube's distal end to facilitate creation of the contraction. It is also possible for the apical tip to be formed in a tapered shape such as a cone, for example, to obtain a smoother insertion of the medical tube set. Tapering the apical tip of the stylet makes it easier for the medical tube set to pass through a constriction in the colon, when for example, the medical tube set is inserted into a colon where a constriction has developed. It is also possible to provide for a tapered apical tip at the distal end of the stylet, in order to reduce the occurrence of colon puncture, by removing the stylet from the tube after the medical tube set has been inserted into the colon. The inner core of the stylet may also be structured as a solid linear member, or as a hollow tubular body. Structuring of the inner core of the stylet as a tubular body enables passage of a guide wire through the inside.

Another structural characteristic of the medical tube set of at least one embodiment of the present invention is structuring of the mobile expansion member as a spherical member.

With a medical tube set having this structure, when the apical tip is engaged with the tube's distal end and the stylet has been pushed in from the posterior end of the tube towards the front end, the mobile expansion member, while positioned in a part of the inner core separated by a predetermined distance from the apical tip, moves together with the inner core towards the distal end of the tube. When this happens, the tube's distal end, which had been in a contracted condition, is pushed radially outwards by the spherical surface of the distal end of the mobile expansion member, and widens. Then, when the mobile expansion member is thrust to the outside from the tube's distal end, the tube's distal end will either maintain its expanded condition or assume a contracted condition.

If the tube's distal end continues in the expanded condition, when the stylet is pulled to the back of the tube, the mobile expansion member will remain positioned in the distal end while the stylet is withdrawn, and the mobile expansion member is positioned such that it comes into contact with the apical tip in the inner core. Then, when the stylet is drawn further backwards, the apical tip will not be subjected to resistance from the tube's aperture rim because the external diameter of the apical tip has been designed to be smaller than or equal to the external diameter of the mobile expansion member, and thus it enters the tube together with the mobile expansion member.

When the stylet is pulled backwards through the tube while the tube's distal end is contracted, the mobile expansion member will remain positioned in the tube's distal end but the stylet will retreat; thus the mobile expansion member is positioned such that it comes into contact with the apical tip in the inner core. Then, when the stylet is pulled farther back, the mobile expansion member is pressed against the inside of the tube via the apical tip, and the spherical surface on its posterior side pushes and widens the tube's distal end radially outward. The mobile expansion member together with the apical tip then enters the tube. In this way, by structuring the mobile expansion member as a spherical member, the structure of the mobile expansion member is simplified, and a reliable operation to remove the stylet is also possible.

Yet another structural characteristic of at least one embodiment of the medical tube set of the present invention is that the mobile expansion member comprises an engagement projection, wherein the distal end engages the engagement concavity of the apical tip. By this means, when the stylet is pushed from the posterior end towards the distal end of the tube, the apical tip and mobile expansion member are thrust from the tube's distal end, and then, when the stylet is pulled towards the posterior end of the tube, the engagement concavity of the apical tip engages with an engagement projection of the mobile expansion member, and thus the apical tip and mobile expansion member become a single unit and move as such. This allows smooth removal of the stylet from the tube.

Yet another structural characteristic of at least one embodiment of the medical tube set of the present invention is that the mobile expansion member comprises an engagement covering that engages the apical tip while the distal end covers at least the posterior portion of the apical tip.

By this means, when the stylet is pushed towards the tube's distal end, the apical tip and mobile expansion member are thrust from the tube's distal end; then when the stylet is pulled towards the posterior end of the tube, the engagement covering of the mobile expansion member covers the posterior end of the apical tip, so the mobile expansion member engages with the apical tip. Thus the apical tip and mobile expansion member become a single unit, and when seen from the direction of movement, the apical tip is covered by the mobile expansion member. This enables smooth removal of the stylet from the tube. In this case, the mobile expansion member may either cover just the posterior end portion of the apical tip, or it may cover the entire apical tip.

Yet another structural characteristic of at least one embodiment of the medical tube set of the present invention is that a provision is made for a stop positioned at a part of the inner core separated by a predetermined distance from the apical tip, such that the mobile expansion member moves between the apical tip and the stop. By this means, the range of movement of the mobile expansion member with respect to the inner core is regulated by a simple structure. The stop is structured either as a large-diameter part formed on the circumference of the inner core, or as a ring shaped member affixed to the circumference of the inner core.

Having described the embodiments of the invention in detail, it will be apparent that modifications and variations are possible without departing from the scope of the invention defined in the appended claims.

When introducing elements of the present invention or the illustrated embodiments thereof, the articles "a", "an", "the" and "said" are intended to mean that there are one or more of the elements. The terms "comprising", "including" and "having" are intended to be inclusive and mean that there may be additional elements other than the listed elements.

As various changes could be made in the above constructions, products, and methods without departing from the scope of the invention, it is intended that all matter contained in the above description and shown in the accompanying drawings shall be interpreted as illustrative and not in a limiting sense.

What is claimed is:

1. A medical tube set from which, after insertion of said tube set into a patient, a stylet may be retracted, comprising:
   a tube for insertion into a patient, and
   a stylet disposed within said tube, said stylet comprising:
      a core unit;
      an apical tip unit attached to a distal end of said core unit and arranged to engage with a distal end of said tube for insertion of said tube and stylet into a patient; and
      an expansion member disposed within said tube which is movable along the core unit to a posterior part of the apical tip unit in the core unit, and such that said expansion member is deployable to expand said distal end of said tube so as to allow retraction of said stylet from said tube;
   wherein said distal end of said tube is tapered; and
   wherein the external diameter of said expansion member is equal to, or larger than, the external diameter of said apical tip unit, and
   wherein said apical tip unit overlaps an edge of said distal end of said tube for insertion of said tube and said stylet into a patient.

2. The medical tube set according to claim 1, wherein said expansion member includes a substantially conical region for expanding said distal end of said tube.

3. The medical tube set according to claim 1, wherein said expansion member is cup-shaped.

4. The medical tube set according to claim 1, wherein said apical tip unit includes a recess at a proximal end thereof for receiving said expansion member.

5. The medical tube set according to claim 1, wherein said stylet includes a first stop unit attached to said core unit for limiting the movement of said expansion member.

6. The medical tube set according to claim 5, wherein said stylet includes a second stop unit positioned distally respective to said first stop unit.

7. The medical tube set according to claim 1 wherein the tube (10) comprises a tube main unit, branch tubes branching off from a proximal end of the tube main unit, and an imaging balloon.

8. The medical tube set according to claim 7 wherein the branch tubes are connected to a suction device or a supply device.

9. The medical tube set according to claim 1 wherein the tube comprises an irrigation side hole and multiple flushing side holes.

10. The medical tube set according to claim 1 further comprising a clamp consisting of an engagement member, a tip, support leaves, a pin bridging the support leaves, and pressure leaves.

11. The medical tube set according to claim 1 wherein the core unit is pushed in a distal direction causing an expansion member located on the core unit to expand a distal end of the tube, or wherein the core unit is pulled in a proximal direction to engage the apical tip unit with the expansion member.

12. The medical tube set according to claim 11 wherein said expansion member is spherical.

13. A method for inserting a medical tube set into a patient comprising the steps of:
   inserting a tube into a patient to a desired position wherein a distal end of said tube is engaged with an apical tip unit of a stylet disposed within said tube;
   pushing a core unit of said stylet in a distal direction causing a mobile expansion member located along said core unit to expand a distal end of said tube;
   pulling said core unit in a proximal direction such that said apical tip unit engages with said expansion member; and
   withdrawing said stylet from said tube.

14. A medical tube set from which, after insertion of said tube set into a patient, a stylet may be retracted, comprising;
   a tube for insertion into a patient, and
   a stylet disposed within said tube, said stylet comprising:
      a core unit;
      an apical tip unit attached to a distal end of said core unit and arranged to engage with a distal end of said tube for insertion of said tube and stylet into a patient; and
      an expansion member disposed within said tube which is movable along the core unit to the posterior part of the apical tip unit in the core unit, and such that said expansion member is deployable to expand said distal end of said tube so as to allow retraction of said stylet from said tube;
   wherein said distal end of said tube is tapered; and
   wherein the external diameter of said expansion member is equal to, or larger than, the external diameter of said apical tip unit, and
   wherein said apical tip unit overlaps an edge of said distal end of said tube for insertion of said tube and said stylet into a patient, and
   wherein said expansion member is spherical.

* * * * *